United States Patent
Kucklick

(10) Patent No.: US 9,526,878 B2
(45) Date of Patent: Dec. 27, 2016

(54) ANTI-EXTRAVASATION SURGICAL PORTAL PLUG

(71) Applicant: Cannuflow, Inc., Campbell, CA (US)

(72) Inventor: Theodore R. Kucklick, Campbell, CA (US)

(73) Assignee: Cannuflow, Inc., Campbell, CA (US)

( * ) Notice: Subject to any disclaimer, the term of this patent is extended or adjusted under 35 U.S.C. 154(b) by 0 days.

(21) Appl. No.: 14/970,221

(22) Filed: Dec. 15, 2015

(65) Prior Publication Data

US 2016/0096007 A1 Apr. 7, 2016

Related U.S. Application Data

(63) Continuation of application No. 14/183,178, filed on Feb. 18, 2014, now Pat. No. 9,211,139, which is a continuation of application No. 11/437,148, filed on May 18, 2006, now Pat. No. 8,652,090.

(51) Int. Cl.
| | |
|---|---|
| *A61M 1/00* | (2006.01) |
| *A61M 27/00* | (2006.01) |
| *A61B 17/00* | (2006.01) |
| *A61B 17/34* | (2006.01) |
| *A61M 39/24* | (2006.01) |
| *A61B 17/16* | (2006.01) |

(52) U.S. Cl.
CPC .......... *A61M 27/00* (2013.01); *A61B 17/0057* (2013.01); *A61B 17/3423* (2013.01); *A61M 39/24* (2013.01); *A61B 17/1684* (2013.01); *A61B 2017/00654* (2013.01); *A61B 2217/005* (2013.01); *A61M 1/008* (2013.01)

(58) Field of Classification Search
CPC .................. A61B 17/12159; A61B 17/0057; A61B 17/00; A61B 17/12022; A61B 17/12172; A61M 27/00; A61M 1/0088; A61M 25/02; A61M 2025/0246; A61M 27/006; A61F 9/00772; A61F 2/0009; A61F 9/0017; A61F 9/00781; A61F 2/147; A61F 2/958; A61F 2/95; A61K 9/0051; A61K 9/0024; A61K 9/0048; A61L 31/16; A61L 27/54
See application file for complete search history.

(56) References Cited

U.S. PATENT DOCUMENTS

| | | | | |
|---|---|---|---|---|
| 5,727,569 | A * | 3/1998 | Benetti et al. | 128/898 |
| 2003/0079329 | A1 * | 5/2003 | Yaron et al. | 29/428 |

\* cited by examiner

*Primary Examiner* — Scott Medway
(74) *Attorney, Agent, or Firm* — K. David Crockett, Esq.; Susan L. Crockett, Esq.; Crockett & Crockett, PC

(57) ABSTRACT

The devices and methods shown provide for the minimization of extravasation during arthroscopic surgery. The anti-extravasation surgical portal plug allows a surgeon to drain excess fluids from the soft tissue surrounding the surgical field during arthroscopic surgical procedures.

5 Claims, 7 Drawing Sheets

ANTI-EXTRAVASATION SURGICAL PORTAL PLUG

This application is a continuation of U.S. application Ser. No. 14/183,178 filed Feb. 18, 2014, now U.S. Pat. No. 9,211,139 which is a continuation of U.S. application Ser. No. 11/437,148 filed May 18, 2006, now U.S. Pat. No. 8,652,090.

FIELD OF THE INVENTIONS

The inventions described below relates to the field arthroscopic surgery and more specifically, to fluid management during arthroscopic shoulder surgery.

BACKGROUND OF THE INVENTIONS

During minimally invasive surgeries, surgical instruments such as trocars, cannulas, and optical medical devices, including endoscopes, cystoscopes, arthroscopes, laparoscopes, etc., are inserted through small incisions or surgical portals in a patient's body or body cavity and manipulated to perform surgical procedures within the patient.

Minimally invasive surgical procedures are safer than open surgery and result in quicker patient recovery, shorter hospital stays, and lower health care costs. Accordingly, minimizing invasiveness continues to be of importance, and there is a continuing need for devices and methods that achieve this objective.

Areas that have benefited from minimally invasive surgical techniques include shoulder and knee surgery. Shoulder and knee surgery have evolved over the last several years from being open surgical procedures to arthroscopic surgical procedures. This evolution is the result of technological advances in equipment, instruments and implants.

During surgery, surgical portals are made into the patient to facilitate surgery and fluid is introduced into the surgical site to expand the joint and control bleeding. One concern involving arthroscopic surgery includes fluid leaking out of open unused surgical portals when surgical instruments are removed. Open portals tend to leak irrigation fluid which gets on the surgery room floor and the surgeon himself. Another concern involving arthroscopic surgery includes extravasation. Extravasation is the collection of interstitial fluid such as blood, irrigation fluids or medications into tissue surrounding an infusion site. Fluid escaping into the soft tissues of the shoulder and the periscapular region can have adverse effects on the patient. Some of these effects include tracheal compression, the accumulation of blood or clots in the joint (hemarthrosis), the forming of blood clots in veins (thrombophlebitis), arterial injury, nerve injury, the compression of blood vessels and nerves surrounding the joint (compartment syndrome), and infection. These effects cause longer recovery time as well as pain and discomfort in patients. Extravasation occurring during surgery can also cause premature collapse of the surgical field forcing surgeons to rush procedures.

Another concern during the performance of surgical procedures is the tendency of surgical instruments to be easily pushed out or removed from surgical portals. Many retention devices have been used to prevent the easy removal of devices during surgery. These devices and methods, however, can cause additional damage and trauma to tissue surrounding the surgical portal. Present tissue retention systems use a series of pointed ridges or threads disposed on the surface of arthroscopic surgical instrument to prevent the instruments from being easily removed from a surgical portal once they are disposed in the surgical portal.

Because of fluid leakage and the effects caused by extravasation and the trauma caused by traditional retention systems, devices and methods are needed to temporarily close unused surgical portals, reduce extravasation during arthroscopic surgery reduce and the trauma potentially caused by retention systems.

SUMMARY

The devices and methods shown below provide for the minimization of fluid leakage and extravasation during arthroscopic surgery. The portal plug allows a surgeon to temporarily close a surgical portal while draining fluids from the soft tissue surrounding the surgical field.

The portal plug is a multi-lumen tube or sheath disposed about an inner core. The proximal portion of the sheath is provided with a handle or grip and a drainage port. The body or central portion of the sheath is provided with a plurality of drainage apertures. Each drainage aperture communicates with one or more of the drainage lumens inside the sheath, thereby allowing fluid to drain from the tissue surrounding the surgical site to sources or sinks located outside the patient. The portal plug allows the surgeon to temporarily close a surgical portal while reducing the amount of fluid extravasation occurring in surrounding tissue. The outer surface of the central portion of the sheath of the portal plug may be embossed with a plurality of cup-shaped depressions, concave pockets or ridges that compose the retention system. When the anti-extravasation sheath is in use, a partial vacuum is produced when tissue surrounding a surgical portal comes in contact with the retention system disposed on the outer surface of the sheath.

DETAILED DESCRIPTION OF THE INVENTIONS

Figure 1:
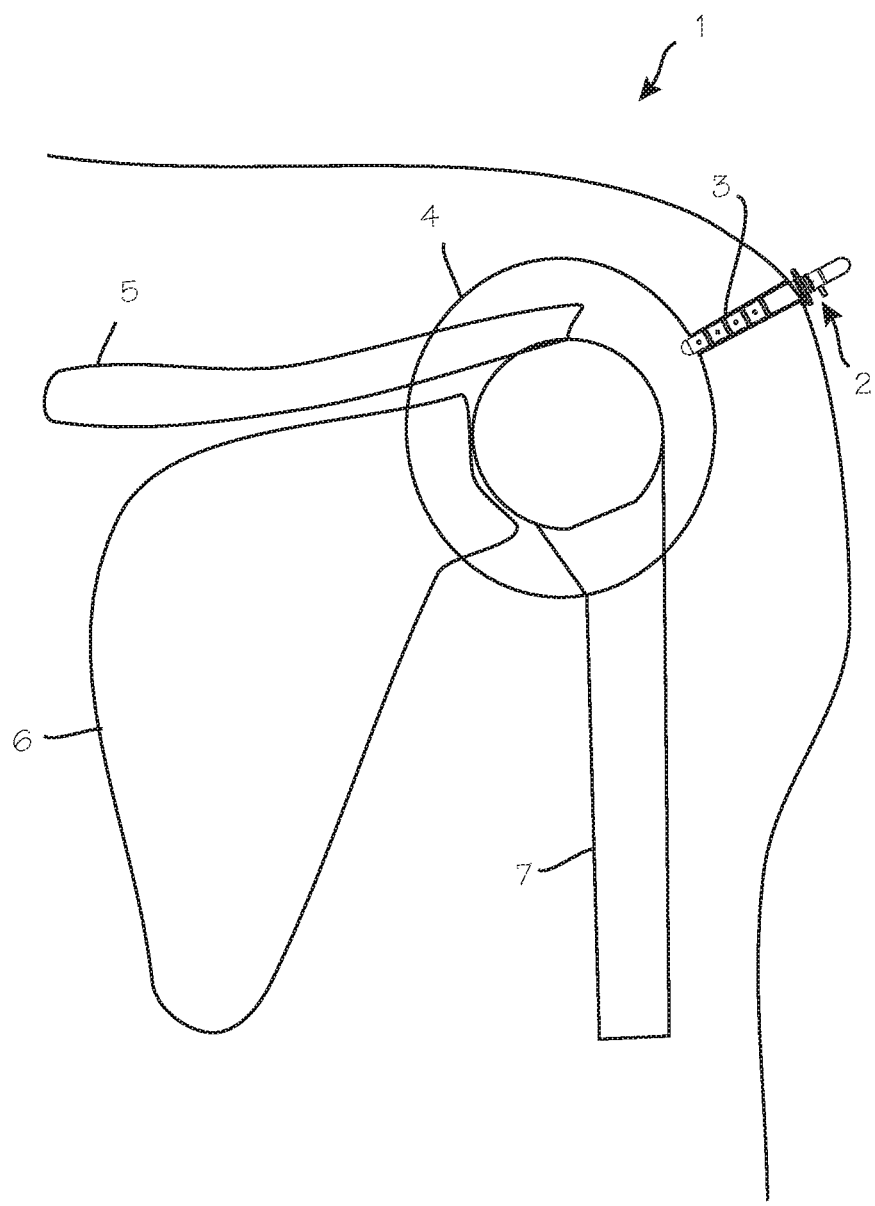
FIG. 1 illustrates a method of performing arthroscopic surgery on a patient using an anti-extravasation surgical portal plug.

FIG. 1 illustrates a method of performing arthroscopic surgery on a patient's shoulder 1 using the anti-extravasation surgical portal plug 2. The portal plug 2 is shown inserted into a surgical portal 3 or incision providing access to the joint capsule 4 of a shoulder of a patient. Various anatomical landmarks are depicted including the patient's clavicle 5, scapula 6 and humerus 7.

During arthroscopic shoulder surgery, the surgeon introduces the arthroscope into the shoulder via a first portal in order to visualize the surgical field. A trimming instrument is introduced through a second portal to remove or trim tissue that the surgeon determines should be removed or trimmed. Optionally, an irrigating instrument may be introduced through a third portal in order to distend the joint, and/or irrigate the surgical field to maintain a clear view. Other arthroscopic instruments used in arthroscopic surgery include endoscopes, awls, picks or shavers. When a surgical instrument is removed from a portal, the portal plug may then be inserted into the surgical portal to prevent fluid leakage and prevent extravasation.

Figure 2:
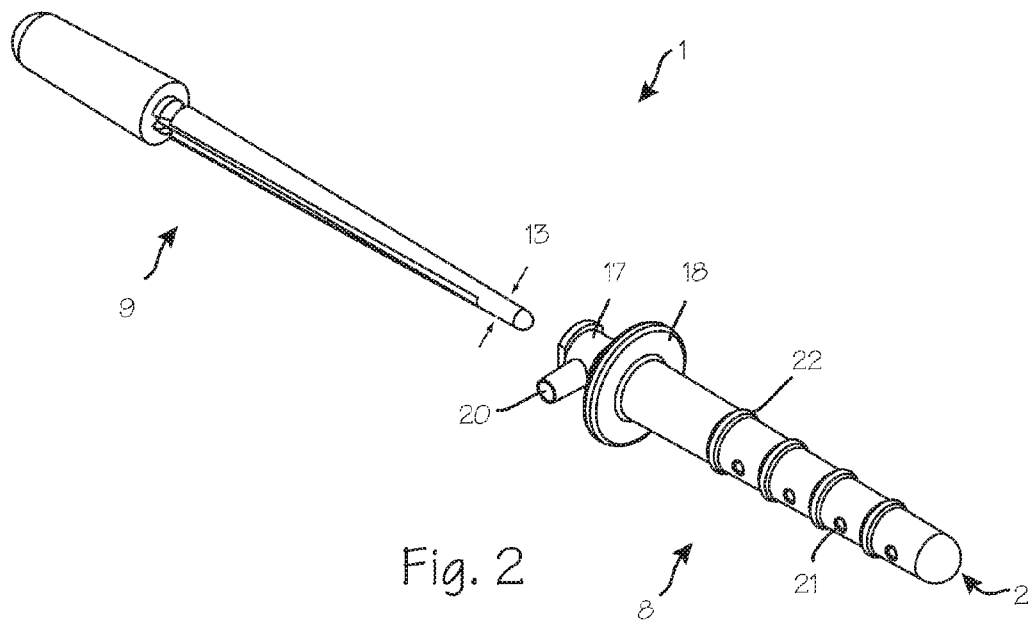
FIG. 2 illustrates an exploded view of the anti-extravasation surgical portal plug.
Figure 3:
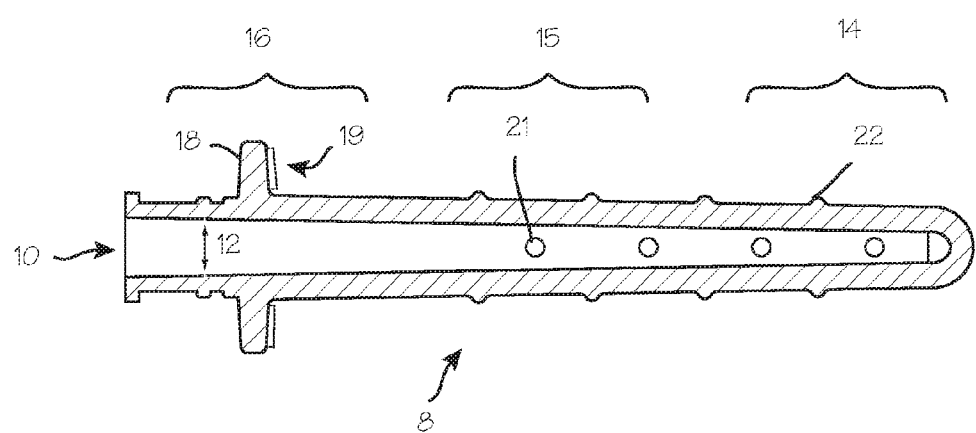
FIG. 3 illustrates a longitudinal sectional view of the anti-extravasation surgical portal plug sheath.

FIG. 2 illustrates an exploded view of surgical portal plug 2 while FIG. 3 illustrates a longitudinal sectional view of a portal plug sheath. The anti-extravasation surgical portal plug comprises a close-ended sheath 8 or tube disposed about an inner core 9. The sheath 8 is a tube of resilient material such as nylon, polycarbonate urethane, polyurethane, polydimethylsiloxane and polyethylene glycol or rubber, characterized by a central lumen 10 and closed at its distal end 11. The inner diameter 12 of the sheath is sized and dimensioned to closely fit over the outer diameter 13 of the inner core 9. The sheath is characterized by a distal portion 14, a central portion 15 and a proximal portion 16. A hub 17 or grip is disposed on the proximal section of the sheath and may be integrally formed with the sheath. The proximal portion 16 of the sheath further comprises a radial flange 18. The flange 18 can be provided with an adhesive layer 19 or surface on its distal bottom surface to assist with holding the sheath in the wound. The flange 18 prevents the plug from entering too deep into the surgical portal. A drainage port 20 in fluid communication with the central lumen 10 is disposed on the proximal section and may be operably coupled to a vacuum source or sink. A proximal section opening is provided in the sheath so the inner core may be inserted. The body or central portion 15 of the sheath contains a plurality of drainage apertures 21. The apertures 21 may be disposed in a series of linear arrays. Each drainage aperture communicates with one or more of the drainage lumens inside the sheath. The drainage apertures 21 are disposed in such a way that they are placed in fluid communication with tissue surrounding a joint capsule or surgical field when the plug is in use. The drainage apertures 21 communicate with one or more drainage lumens 33 disposed inside the plug which allows fluid to drain from the tissue surrounding the capsule to vacuum sources or sinks located outside the patient through the drainage port. The drainage port 20 can be adapted for coupling to an active or passive vacuum source or sink. The outer surface of the proximal section of the plug is corrugated or provided with ridges 22 to prevent the sheath or instrument from being unintentionally forced out of the operating field. The ridges 22 of the tissue retention feature are circumferentially disposed around the portal plug 2 and may be in the shape of straight ridges extending radially outward as illustrated in FIG. 2. The ridges of the tissue retention feature may also be in the shape of a threaded screw or other shape suitable to prevent the plug 2 from being easily removed from a surgical portal once the plug 2 is disposed within a surgical portal. The distal end of the sheath is provided with a rounded, arcuate or frustoconial shaped tip.

Figure 4:
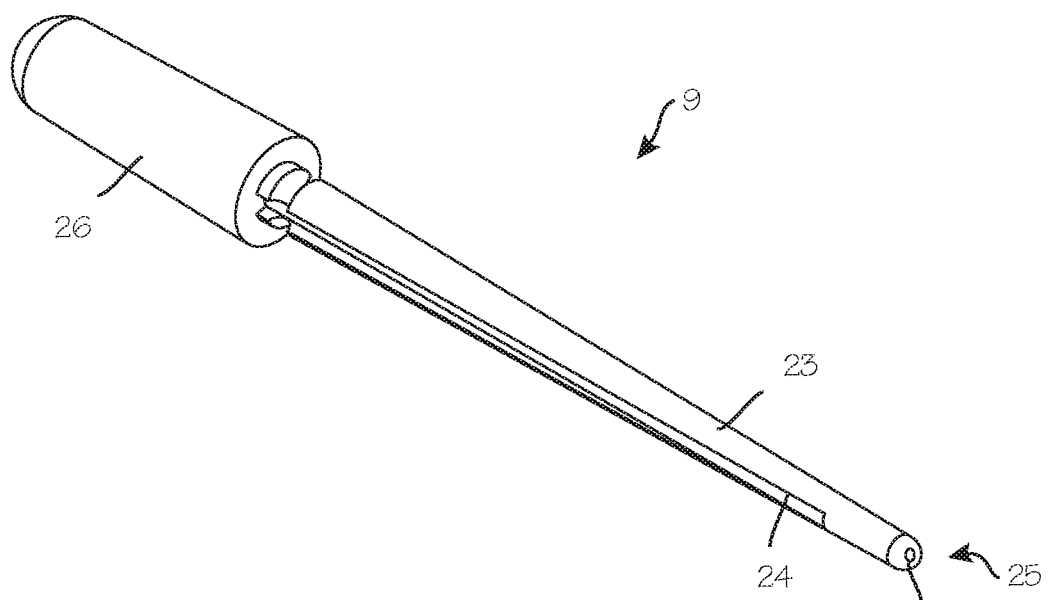
FIG. 4 illustrates the inner core for use in the anti-extravasation surgical portal plug.

FIG. 4 illustrates the inner core 9 for use in conjunction the portal plug 2. The inner core 9 comprises a rigid shaft 23 having one or more grooves, channels or flutes 24 disposed longitudinally along the core's outer surface. The core is provided with a frustaconical or arcuate shaped tip 25 disposed on its distal end. A finger grip 26 or handle is disposed on the proximal portion of the inner core and may be integrally formed with the inner core. The inner core 9 may also be provided with a center lumen 27 allowing the core to drain fluid from a surgical site.

Figure 5:
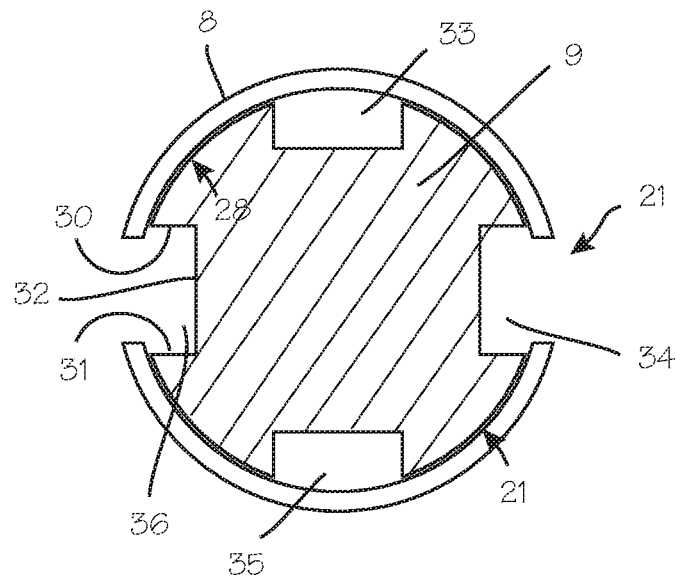
FIG. 5 shows a radial cross-sectional view of the anti-extravasation surgical portal plug using the inner surface of the sheath wall with the outer surface of the inner core to form drainage lumens.

FIG. 5 shows a radial cross-sectional view of portal plug 2 with the inner core 9 using the inner surface of the sheath wall with the outer surface of the inner core to form drainage lumens. The inner surface 28 of the wall of the sheath and the outer surface 29 of the inner core forms a seal and the side walls 30,31 and bottom walls 32 of the flutes 24 and the wall of the tube create the longitudinal drainage lumens 33, 34, 35 and 36. One or more drainage apertures 21 are disposed on the outer surface of the body or central portion 15 of the sheath. The drainage apertures are in fluid communication with the one or more drainage lumens 33, 34, 35 and 36. The drainage lumens 33, 34, 35 and 36 and run longitudinally along the sheath and are sized and dimensioned to accommodate fluid outflow from tissue surrounding a surgical site. The size of the drainage apertures can be used to control the percolation rate of the sheath 8.

Figure 6:
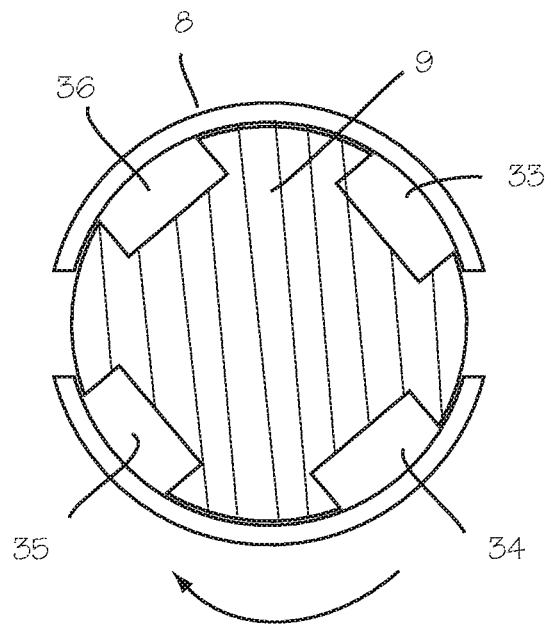
FIG. 6 shows the inner core rotated within the sheath.

When the portal plug 2 is in use, inner core 9 containing longitudinal grooves is disposed in the central lumen 10 of the sheath. The core 9 may or may not be covered by a secondary protective sheath prior to insertion. Once inserted, the outer surface 29 of the core frictionally engages the inner surface 28 of the sheath. The force of the outer surface 29 of the core pushes against the inner surface of the sheath. Outer drainage lumens 33, 34, 35 and 36 are created by the flutes 24 and the inner surface of the outer wall of the sheath. The seals formed by the contact between the sheath and the outer surface of the core prevent fluids from flowing between the outer drainage lumens 33, 34, 35 and 36. The outer drainage lumens 33, 34, 35 and 36 facilitate the outflow of fluids from tissue surrounding a surgical site through the drainage apertures in the central portion of the sheath. When a user wants to stop or reduce the outflow of fluid from an open surgical portal not in use by another surgical instrument, the user inserts the portal plug 2 into the surgical portal. The portal plug is placed in fluid communication with tissue surrounding the surgical field through the drainage apertures 21 in the sheath. The outflow of fluid is regulated or stopped by rotating the inner core within the sheath as shown in FIG. 6. This reduces or eliminates the amount of drainage lumens placed in fluid communication with the drainage apertures.

Figure 7:
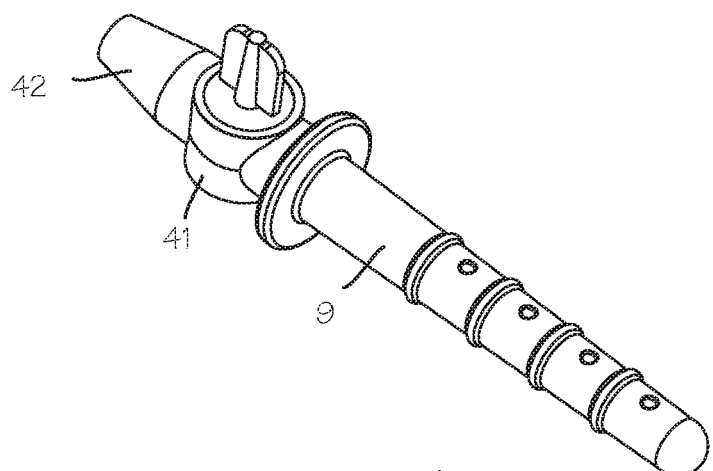
FIG. 7 illustrates the sheath with an alternative control system.

The drainage of fluid from tissue may also be regulated by using a portal plug with an alternative method of control. FIG. 7 illustrates the sheath 8 or close-end tube of FIG. 2 having a control valve disposed on its proximal end. In FIG. 7, a valve 41 or other fluid control means is disposed on the proximal section of the sheath 8. The valve 41 is placed in fluid communication with the sheath's central lumen 10 and a drainage port 42. The drainage port 42 is operably coupled to a vacuum source or sink to actively or passively facilitate fluid removal.

Figure 8:
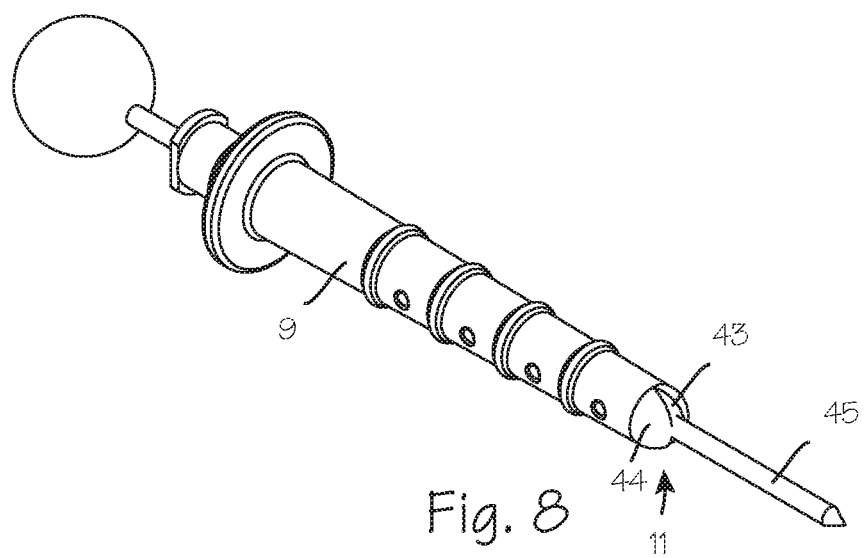
FIG. 8 shows the sheath having a membrane valve disposed in its distal end.

FIG. 8 shows the sheath 8 of FIGS. 2 and 3 having a membrane valve 43 or seal disposed in its distal end 11. The wall 44 of the sheath on the distal end creates a fluid resistant seal that seals against fluid pressure but allows passage of arthroscopic surgical instruments 45 used in the arthroscopic procedures. The wall comprises self-sealing silicone capable of accommodating the surgical instrument by resiliently expanding and conforming around the surgical instrument when the surgical instrument is forced through the bottom wall and resiliently closing to a fluid tight seal when the surgical instruments are removed. Thus, the bottom wall or fluid resistant seal allows for insertion of various instruments, catheters and elongate medical devices while functioning as a membrane seal that minimizes fluid leakage. The bottom wall may also be provided with a slit (single or cross-cut) to facilitate insertion and removal of the surgical instruments or other medical instruments.

Figure 9:
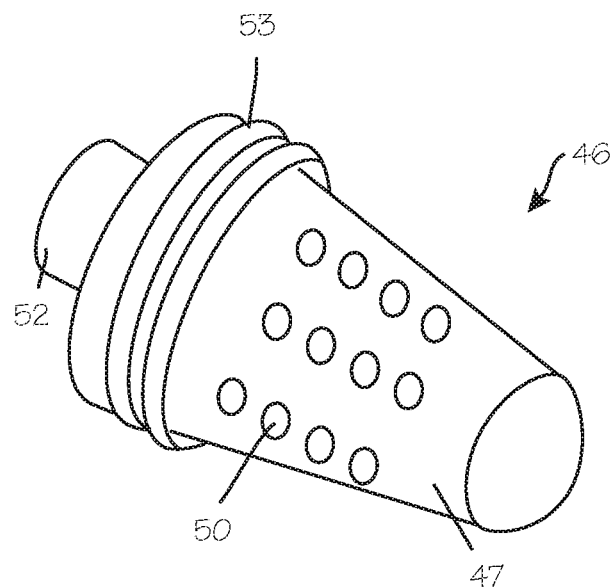
FIG. 9 illustrates an alternative embodiment of an anti-extravasation surgical portal plug.
Figure 10:
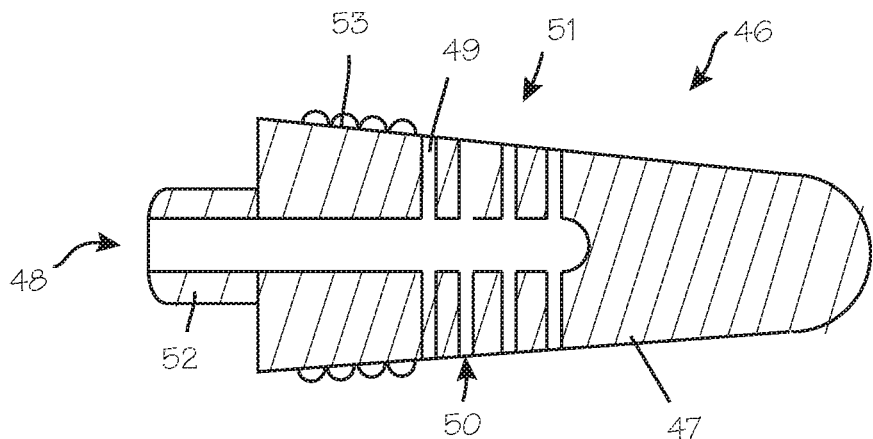
FIG. 10 illustrates a longitudinal cross-section of the alternative embodiment of the anti-extravasation surgical portal plug.

FIG. 9 illustrates an alternative embodiment of a surgical portal plug 46 while FIG. 10 illustrates a longitudinal cross-section of the surgical portal plug 46. Here, the plug 46 comprises a frustoconical body 47 having a coaxial central lumen 48. The central lumen 48 comprises blind hole or bore that stops proximal to distal end of the frustoconical body. Drainage lumens 49 extend radially outward from the center lumen placing the center lumen in fluid communication with drainage apertures 50 disposed along the central portion 51 of the plug. The drainage apertures are disposed in such a way that they are placed in fluid communication with tissue surrounding a joint capsule or surgical field when the plug is in use. The drainage apertures 50 communicate with one or more drainage lumens 49 disposed inside the plug, thereby allowing fluid to drain from the tissue surrounding the joint capsule to sources or sinks located outside the patient through a drainage port in fluid communication with the central lumen 48 disposed on the proximal section of the plug. A cylindrical shaped finger grip 52 extends proximally from the proximal section of the frustoconical body and can be operably coupled to a vacuum source.

The outer surface of the proximal section of the plug is corrugated or provided with ridges 53 to prevent the sheath or instrument from being unintentionally forced out of the operating field. The ridges of the tissue retention feature are circumferentially disposed around the plug and may be in the shape of straight ridges extending radially outward as illustrated in FIG. 10. The ridges of the tissue retention feature may also be in the shape of a threaded screw or other shape suitable to prevent the plug from being easily removed from a surgical portal once the plug is disposed within a surgical portal. The integrally structured surgical plug 2 may be manufactured from biocompatible polymers such as silicone.

The portal plug 2 can be part of a complete fluid management system comprising a fluid source, vacuum source, arthroscopic surgical pump and control system. An over pressure valve can be operably coupled to the plug to allow a drainage lumen in the device to open and drain the joint if the joint is over-pressurized by an arthroscopic pump.

Figure 11:
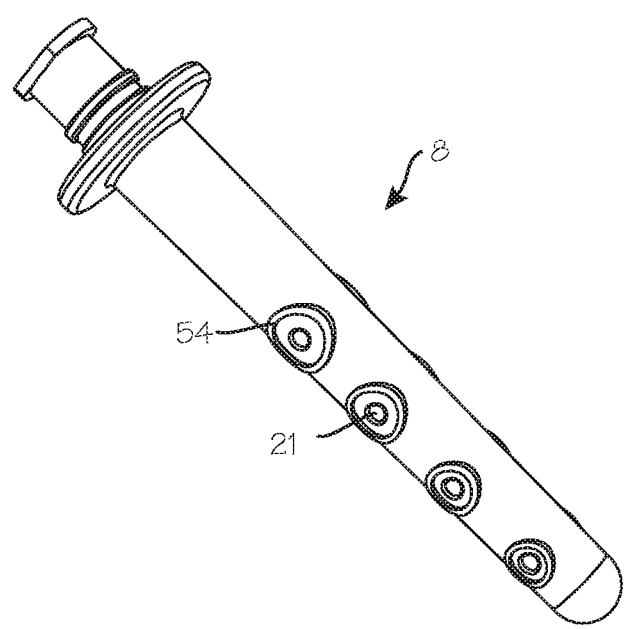
FIG. 11 illustrates an anti-extravasation surgical portal plug having a sheath with a retention system.

FIG. 11 illustrates the anti-extravasation surgical portal plug having a sheath 8 with a retention system. The outer surface of the sheath 8 shown in FIGS. 2 through 8 may further comprise a retention system 54 having a plurality of atraumatic retention features including cup-shaped depressions, bellow-shaped extensions, concave pockets or a series of ridges. The retention system may be embossed in the outer surface of the sheath or the retention system may comprise separate devices coupled to the outer surface of the sheath. The retention system 54 is sized and dimensioned to function as a plurality of suction-cups and has rounded atraumatic edges. When the sheath 8 with the retention system 54 is in use, tissue is drawn to the outer surface of the sheath 8 by the drainage apertures 21. A partial vacuum is produced when the retention features of the retention system disposed on the outer surface of the sheath come in contact with tissue surrounding the surgical portal. The tissue retention system 54 may be disposed on our other anti-extravasation devices such as those disclosed in our U.S. patent application Ser. No. 11/335,077, filed Jan. 18, 2006 and U.S. patent application Ser. No. 11/346,764, filed Feb. 3, 2006 both of which applications are fully incorporated in their entirety by reference. The vacuum produced by the retention features prevents the sheath from being easily removed from the surgical portal while preventing the additional trauma induced by traditional retention features.

While the preferred embodiments of the devices and methods have been described in reference to the environment in which they were developed, they are merely illustrative of the principles of the inventions. Other embodiments and configurations may be devised without departing from the spirit of the inventions and the scope of the appended claims.

I claim:

1. A method of performing arthroscopic surgery, said method comprising:
    forming a surgical portal in the body of a patient;
    providing an arthroscopic instrument suitable for performing an arthroscopic surgical procedure;
    inserting the arthroscopic instrument into the surgical portal;
    performing an arthroscopic surgical procedure;
    providing a surgical portal plug, said plug comprising:
        a close-ended tube characterized by a distal portion, a central portion, a proximal portion and a central lumen, said central lumen terminating proximal to the distal end of the tube;
        a plurality of drainage apertures disposed on the central portion of the tube on the tube outer surface;
        a plurality of drainage lumens disposed on the central portion of the close-ended tube in fluid communication with the central lumen and the drainage apertures, said drainage lumens extending radially outward from the central lumen; and
        a retention system disposed about an outer surface of the tube;
    removing the arthroscopic instrument;
    inserting the portal plug into the surgical portal.

2. The method of claim 1 wherein the retention system comprises a plurality of retention features consisting of a series of ridges circumferentially disposed around the proximal portion of the tube.

3. The method of claim 1 wherein the retention system comprises separate devices coupled to the outer surface of the tube.

4. The method of claim 1 wherein the retention system comprises a plurality of retention features consisting of cup-shaped depressions with atraumatic edges, each of the plurality of cup-shaped depressions positioned to surround each of the plurality of drainage apertures.

5. The method of claim 1 wherein the retention system comprises a plurality of retention features consisting of ridges disposed around the proximal portion of the tube, wherein the retention feature ridges are in the shape of a threaded screw.

* * * * *